United States Patent [19]

Kappel

[11] Patent Number: 5,749,109
[45] Date of Patent: May 12, 1998

[54] INFLATABLE BLANKET HAVING SELECTIVE AIR FLOW PATTERNS

[75] Inventor: Thomas F. Kappel, St. Louis, Mo.

[73] Assignee: Mallinckrodt Medical, Inc., St. Louis, Mo.

[21] Appl. No.: 834,383

[22] Filed: Apr. 16, 1997

Related U.S. Application Data

[63] Continuation of Ser. No. 544,907, Oct. 18, 1995, abandoned.

[51] Int. Cl.[6] ............................................. A61B 5/00
[52] U.S. Cl. .................. 5/423; 5/502; 607/104; 62/259.3; 165/46
[58] Field of Search .................. 5/421, 423, 482, 5/502; 607/104; 62/259.3, 261; 126/204; 165/46

[56] References Cited

U.S. PATENT DOCUMENTS

| | | |
|---|---|---|
| 630,565 | 8/1899 | Safran . |
| 1,291,191 | 1/1919 | Semple . |
| 1,590,522 | 6/1926 | Kalman . |
| 1,777,982 | 10/1930 | Popp . |
| 2,093,834 | 9/1937 | Gaugler . |
| 2,110,022 | 3/1938 | Kliesrath . |
| 2,122,964 | 7/1938 | Sweetland . |
| 2,235,966 | 3/1941 | Summers . |
| 2,512,559 | 6/1950 | Williams . |
| 2,601,189 | 6/1952 | Wales, Jr. . |
| 2,617,915 | 11/1952 | Blair . |
| 2,700,165 | 1/1955 | Talisman . |
| 2,706,988 | 4/1955 | Weber . |
| 2,791,168 | 5/1957 | Mauch . |
| 2,834,033 | 5/1958 | O'Brien . |
| 2,998,817 | 9/1961 | Armstrong . |
| 3,034,132 | 5/1962 | Landsberger et al. . |
| 3,307,554 | 3/1967 | Thornton et al. . |
| 3,308,850 | 3/1967 | Gill . |
| 3,610,251 | 10/1971 | Sanderson . |
| 3,674,034 | 7/1972 | Hardy . |
| 3,740,777 | 6/1973 | Dee . |
| 3,757,366 | 9/1973 | Sacher . |
| 3,844,339 | 10/1974 | Kranz . |
| 4,026,299 | 5/1977 | Sauder . |
| 4,094,357 | 6/1978 | Sgroi . |
| 4,398,535 | 8/1983 | Guibert . |
| 4,457,295 | 7/1984 | Roehr . |
| 4,572,188 | 2/1986 | Augustine et al. . |
| 4,653,131 | 3/1987 | Diehl . |
| 4,660,388 | 4/1987 | Greene, Jr. ............................ 5/423 X |
| 4,777,802 | 10/1988 | Feher . |
| 4,807,644 | 2/1989 | Sandhaus . |
| 4,867,230 | 9/1989 | Voss ..................................... 607/104 X |
| 4,959,877 | 10/1990 | Covil . |
| 4,997,230 | 3/1991 | Spitalnick . |
| 5,022,110 | 6/1991 | Stroh . |
| 5,044,364 | 9/1991 | Crowther . |
| 5,097,548 | 3/1992 | Heck et al. . |
| 5,106,373 | 4/1992 | Augustine et al. . |
| 5,125,238 | 6/1992 | Ragan et al. . |

(List continued on next page.)

FOREIGN PATENT DOCUMENTS

| | | |
|---|---|---|
| 1325484 | 12/1993 | Canada . |
| 0311336 | 4/1989 | European Pat. Off. . |
| 149244 | 11/1931 | Switzerland . |
| 85 03216 | 8/1985 | WIPO . |
| 94 03131 | 2/1994 | WIPO . |
| 95 20371 | 8/1995 | WIPO . |
| 95 35077 | 12/1995 | WIPO . |
| 96 03098 | 2/1996 | WIPO . |

*Primary Examiner*—Michael F. Trettel
*Attorney, Agent, or Firm*—Rothwell, Figg, Ernst & Kurz, p.c.

[57] ABSTRACT

The present invention relates to blankets for use with forced air convection systems, wherein the blankets include means to provide air through selective areas of the lower sheet of the blanket. In particular, perforations are provided through the lower sheet of the blanket over only selective areas, such that air exits toward only those portions of a patient which are covered by areas of the blanket having perforations.

3 Claims, 2 Drawing Sheets

U.S. PATENT DOCUMENTS

| | | |
|---|---|---|
| 5,165,400 | 11/1992 | Berke . |
| 5,184,612 | 2/1993 | Augustine .............................. 5/482 X |
| 5,265,599 | 11/1993 | Stephenson .......................... 105/46 X |
| 5,300,098 | 4/1994 | Philipot . |
| 5,300,100 | 4/1994 | Hickle et al. . |
| 5,300,101 | 4/1994 | Augustine et al. . |
| 5,300,102 | 4/1994 | Augustine et al. . |
| 5,304,213 | 4/1994 | Berke et al. . |
| 5,304,217 | 4/1994 | Stephenson et al. . |
| 5,318,568 | 6/1994 | Kaufmann et al. . |
| 5,324,320 | 6/1994 | Augustine et al. . |
| 5,336,250 | 8/1994 | Augustine . |
| 5,343,579 | 9/1994 | Dickerhoff et al. . |
| 5,350,417 | 9/1994 | Augustine . |
| 5,360,439 | 11/1994 | Dickerhoff et al. . |
| 5,384,924 | 1/1995 | Dickerhoff et al. . |
| 5,392,847 | 2/1995 | Stephenson . |
| 5,405,370 | 4/1995 | Irani . |
| 5,405,371 | 4/1995 | Augustine et al. . |
| 5,408,712 | 4/1995 | Brun . |
| 5,443,488 | 8/1995 | Namenye et al. . |
| 5,632,769 | 5/1997 | Kappel et al. .......................... 5/423 X |
| 5,643,337 | 7/1997 | Kappel et al. .......................... 5/423 X |

INFLATABLE BLANKET HAVING SELECTIVE AIR FLOW PATTERNS

This is a continuation of application Ser. No. 08/544,907, filed Oct. 18, 1994, now abandoned.

BACKGROUND

Hypothermia is a condition of subnormal body temperature and presents serious consequences to the patient suffering therefrom. It has been shown that nearly seventy five percent of all patients who undergo surgical procedures develop hypothermia. This equates to approximately fourteen million patients a year in the United States alone. The hypothermic condition is brought on by many factors including anesthesia, the air conditioning of the operating room, and the infusion of cold blood, I-V solutions, or irrigating fluids.

Several methods and products have been developed to help prevent hypothermia from occurring; such as the use of infrared lamps, cotton blankets, and warm water mattresses. However, none of these methods and products have proven completely successful. In fact, it has been shown that these methods and products can not even prevent the patients from losing their endogenous heat. (See Journal of Post Anesthesia Nursing, Vol. 5, No. 4, August 1990, pp 254–263).

Another method of helping to prevent hypothermia that has proven very effective is the use of forced warm air convection. As early as 1937, a refrigeration blanket using cold air convection was suggested in U.S. Pat. No. 2,093,834 to Gaugler. This blanket included a plurality of layers for channeling airflow from an inlet port. Non-inflatable portions were provided around the periphery of the blanket to secure the blanket around the body.

U.S. Pat. No. 2,512,559 to Williams also relates to a blanket for providing cooled air to a person. The blanket in Williams comprised a plurality of thin sheets of material connected together at a plurality of discrete locations and connected together in a continuous line about the peripheral edge. An air inlet was provided to communicate with space between the sheets to allow cool air to be supplied thereto.

In U.S. Pat. No. 4,572,188 to Augustine, et al., a forced air convection system which can supply either cool or warm air to a blanket is described. The blanket in Augustine, et al. comprises a plurality of inflatable hollow tubes having their interiors connected together through transverse openings. An entry port is provided in the upper surface of the blanket for admitting the cool or warm air and small exit ports are provided through the lower surface to allow the cool or warm air to flow out toward a body covered by the blanket.

Other patents relating to the supply of cool or warm air to a person through an inflatable blanket include U.S. Pat. Nos. 4,660,388 to Greene, Jr.; 4,777,802 to Feher; and 4,867,230 to Voss; 5,125,238 to Ragan et al; 5,300,100 to Hickle et al; 5,300,102 to Augustine et al; 5,324,320 to Augustine et al; 5,343,579 to Dickerhoff et al; 5,360,439 to Dickerhoff et al; and 5,384,924 to Dickerhoff et al. Each of these patents describe blankets having various attributes and configurations to supply cool or warm air to the person.

While there are a number of patents noted above and others not mentioned which relate to inflatable blankets for use in supplying cool or warm air to a patient, there remains a need in the art for improvements to forced air convection systems.

Objects Of The Invention

It is one object of the present invention to provide a blanket for a forced air convection system which allows air to be directed only toward the patient, and not to areas around the patient.

It is another object of the present invention to provide a blanket for a forced air convection system which includes means for selectively providing air to portions of a patient's body.

Summary Of The Invention

The above objects and others are accomplished according to the present invention by providing a blanket for a forced air convective system which includes exit perforations arranged in selective patterns.

DETAILED DESCRIPTION OF THE INVENTION

Figure 1:
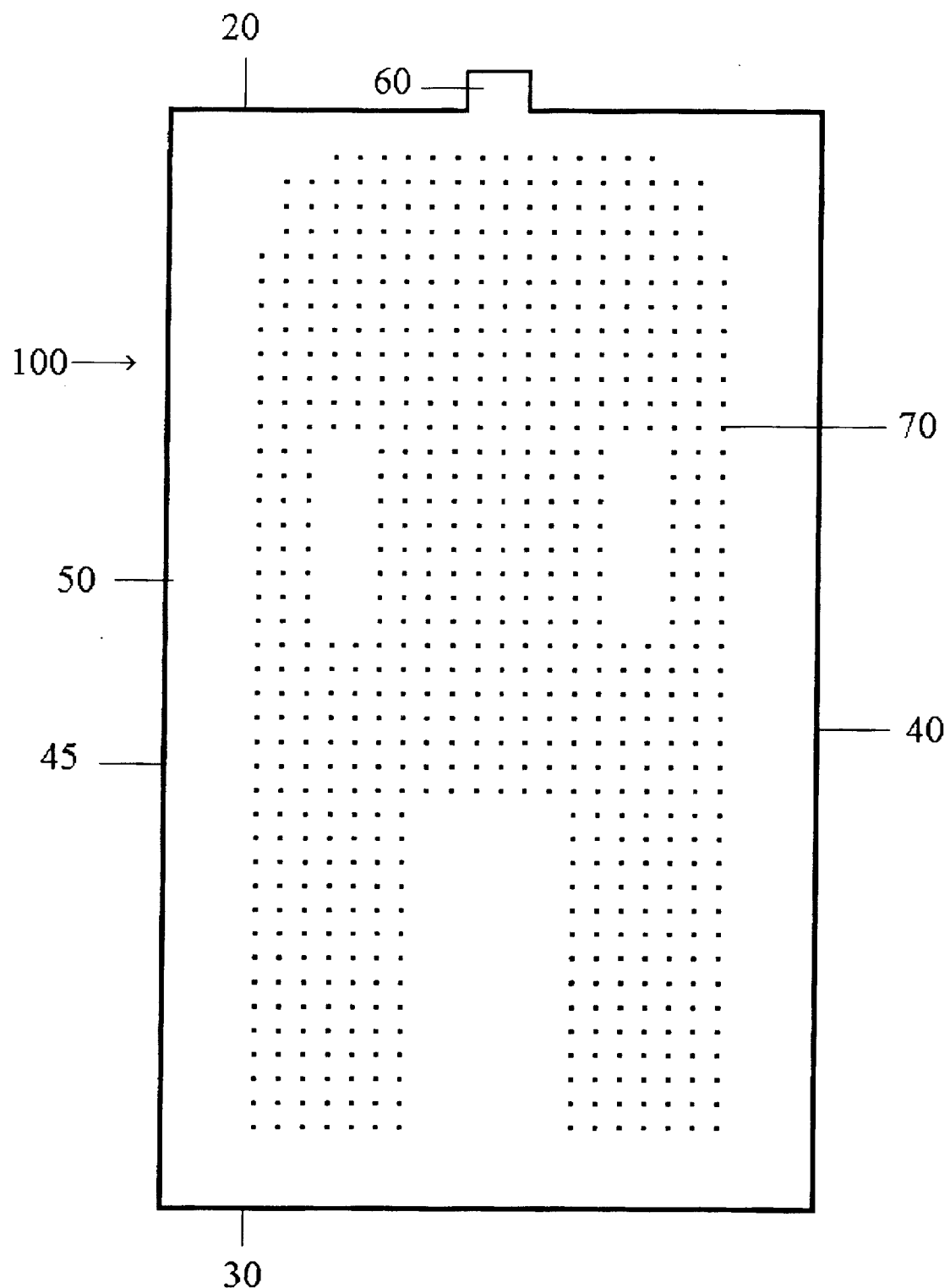
FIG. 1 is a plan view of a blanket for a forced air convection system according to one embodiment of the present invention.

FIG. 1 is a plan view of a blanket, generally designated by reference numeral 10, for a forced air convection system, according to one embodiment of the present invention. In particular, blanket 10, includes an upper or head end 20, a lower or foot end 30, and two sides 40, 45. The blanket 10, further includes an upper sheet of material (not visible), and a lower sheet of material 50. The upper sheet and lower sheet 50, are sealed together around respective peripheral edges to form a cavity therebetween, which may be inflated by introduction of air from an appropriate source. The upper sheet and lower sheet 50, may further be connected together in any one of several desirable configurations, such as spot welds, interconnected columns, interconnected tubes, etc. The blanket 10, includes at least one inlet port 60, for attachment to a source of forced air which will be used to inflate the blanket 10, and provide either warming or cooling air to the patient. As shown in FIG. 1, the inlet port 60, is formed along one end of the blanket 10. However, other configurations are equally acceptable and are within the scope of the present invention, as will be further discussed below. The lower sheet of the blanket 10, includes a plurality of perforations or small exit holes 70, formed therethrough which allow air to escape from the blanket 10, toward a patient.

In order to provide heated or cooled air selectively only to the patient, the perforations 70, are provided in a selective pattern through the lower sheet 50. In particular, as shown in FIG. 1, the perforations 70, are arranged in the general shape of a patient's body.

Figure 2:
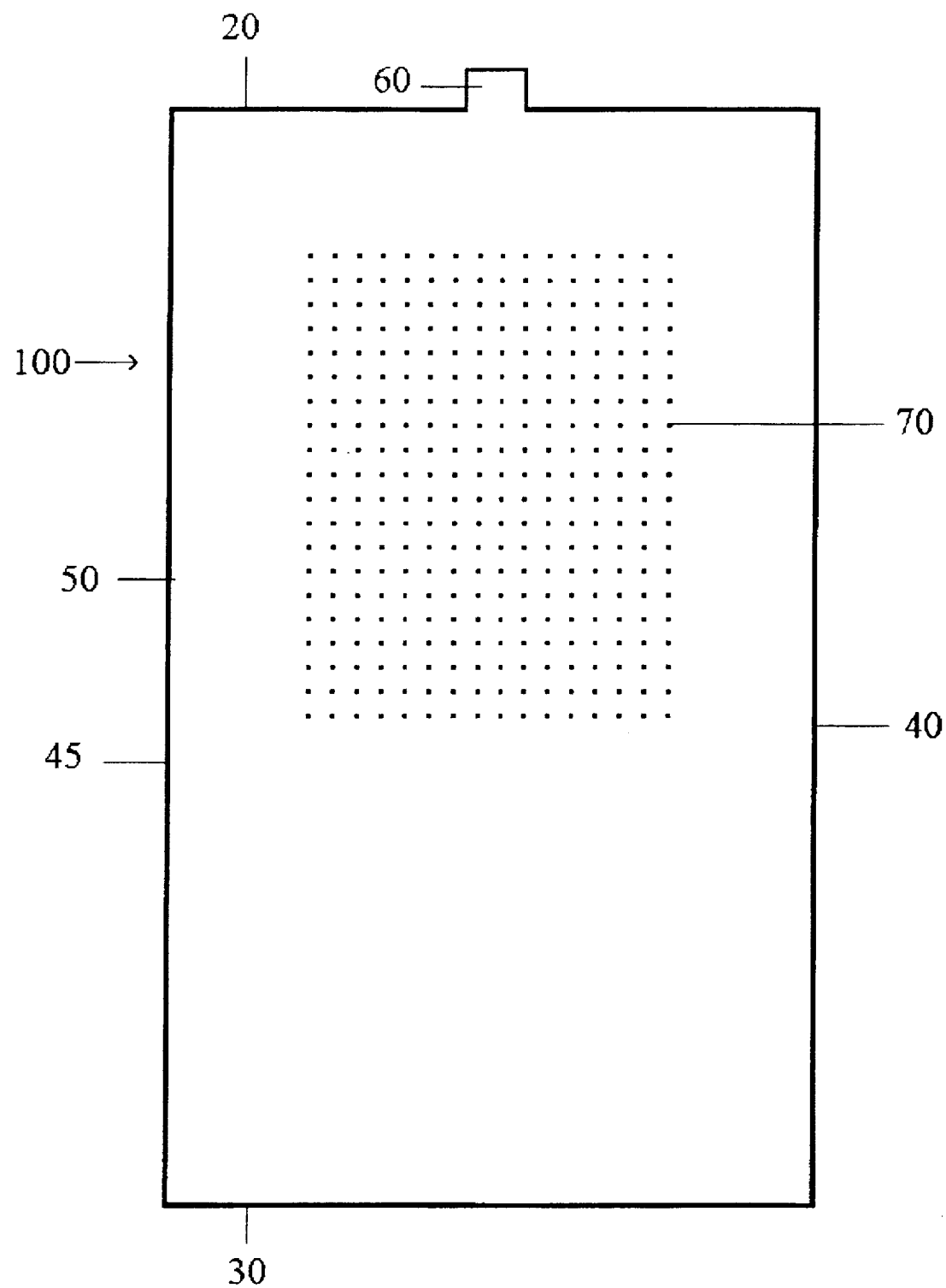
FIG. 2 is a plan view of a blanket for a forced air convection system according to a further embodiment of the present invention.

In addition, it is often desirable to provide heated or cooled air to a selective portion of a patient. Therefore, as shown in FIG. 2, the perforations 70, are provided in a limited, and selected pattern through the lower sheet 50. In particular, as shown in FIG. 2, the perforations 70, are provided only in an area which will cover the chest of a patient.

The present invention relates to any number of patterns of perforations. In addition, perforations may be provided only over one area or may be provided over multiple areas for selectively providing heated or cooled air to directly to those areas of a patient which the perforations cover.

By providing perforations only through selective areas of the lower sheet of the blanket, it is possible to provide heating or cooling to a patient in a more efficient manner. In particular, when perforations are provided over the entire surface area of the lower sheet, air provided through perforations not directly covering a patient may not add significantly to the heating or cooling of the patient. Providing selectively patterned perforations in accordance with the present invention assures that the greatest amount of heating or cooling air will be provided directly to the patient.

The blankets shown in FIGS. 1 and 2 represent full body blankets but the present invention would be equally applicable to blankets intended to cover only portions of the patient, such as an upper body blanket or a lower body blanket. The blankets according to the present invention are also equally useful in both adult and pediatric sizes. Additionally, the blankets according to the present invention may be used equally effectively in either the operating room or in other areas of the hospital, such as the PACU. Moreover, as noted, the blankets according to the present invention may be used to provide either warming or cooling to a patient.

As noted above, the inlet port as shown in FIGS. 1 and 2, is located at a corner of the blanket. However, the inlet port may be located at almost any position which allows the blanket to be easily inflated. For example, the inlet port may be provided along any edge of the blanket or through the upper or lower sheet of the blanket at a location spaced away from the edge of the blanket. In addition, multiple inlet ports may be provided to increase the versatility of the blanket.

The blankets of the present invention may be formed of any suitable material capable of being sealed together at selected positions and having sufficient strength to allow inflation and adequate air distribution within the inflated portion. Such materials include plastics, non-woven wood pulp compositions, laminated plastic and wood pulp materials, and combinations thereof.

The foregoing has been a description of certain preferred embodiments of the present invention, but is not intended to limit the invention in any way. Rather, many modifications, variations and changes in details may be made within the scope of the present invention.

What is claimed is:

1. An inflatable blanket for a forced air convection system comprising:

an upper sheet of material having a generally rectangular shape with an upper end, a lower end and two sides;

a lower sheets of material having a generally rectangular shape with an upper end, a lower end and two sides;

wherein said upper sheets and said lower sheet are sealed together around their peripheral edges at their respective upper ends, lower ends and sides, to create a full body blanket with an inflatable cavity having an upper end, a lower end and two sides therebetween;

an inflation port connecting said inflatable cavity with the atmosphere and through which inflation medium may be introduced to side inflatable cavity to inflate said blanket; and wherein said lower sheet includes a plurality of perforations formed therethrough which are arranged in a specific pattern to allow air to exit only toward selective portions of a patient's body, said lower sheet having perforations only in said specific pattern, and said specific pattern being selected from the group consisting of perforations only in an area of said lower sheet which will cover a patient's chest, and perforations in an area of said lower sheet only in a pattern having said patient's general body shape.

2. A blanket according to claim 1, wherein said perforations are provided in the general shape of a patient's body.

3. A blanket according to claim 1, wherein said perforations are provided only in an area which will cover the chest of a patient.

* * * * *

UNITED STATES PATENT AND TRADEMARK OFFICE
CERTIFICATE OF CORRECTION

PATENT NO. : 5,749,109
DATED : May 12, 1998
INVENTOR(S) : Thomas F. Kappel et al.

Page 1 of 1

It is certified that error appears in the above-identified patent and that said Letters Patent is hereby corrected as shown below:

<u>Title page,</u>
Item [75], Inventors, add -- Scott D. Dickerhoff and Dennis S. Chivetta --.

Signed and Sealed this

Twenty-seventh Day of July, 2004

JON W. DUDAS
*Acting Director of the United States Patent and Trademark Office*